(12) United States Patent
Kollar

(10) Patent No.: US 7,034,189 B1
(45) Date of Patent: Apr. 25, 2006

(54) PREPARATION OF DIALKYL PEROXIDES

(75) Inventor: John Kollar, Wyckoff, NJ (US)

(73) Assignee: Redox Technologies Inc., Winslow, NJ (US)

( * ) Notice: Subject to any disclaimer, the term of this patent is extended or adjusted under 35 U.S.C. 154(b) by 1826 days.

(21) Appl. No.: 08/567,564

(22) Filed: Dec. 5, 1995

(51) Int. Cl.
*C07C 409/00* (2006.01)

(52) U.S. Cl. .................. 568/561; 568/578; 568/568

(58) Field of Classification Search .......... 568/561, 568/578, 568
See application file for complete search history.

(56) References Cited

U.S. PATENT DOCUMENTS

| | | | | |
|---|---|---|---|---|
| 3,308,163 A | * | 3/1967 | McKellin | ................ 568/568 |
| 4,810,809 A | * | 3/1989 | Sanderson et al. | .......... 549/529 |
| 5,288,919 A | * | 2/1994 | Faraj | ................ 568/578 |
| 5,312,998 A | * | 5/1994 | Liotta et al. | ................ 568/578 |
| 5,345,009 A | * | 9/1994 | Sanderson et al. | ........ 568/909.8 |

\* cited by examiner

*Primary Examiner*—Porfirio Nazario-Gonzalez

(57) ABSTRACT

A process is disclosed for the preparation of a dialkyl peroxide comprising reacting one or more members selected from the group consisting of an alkylating alcohol of the formula ROH, and an olefin of the formula $(R^2)(R^{2a})C=C(R^3)(R^{3a})$, wherein R is $C_1$–$C_{10}$ allyl, and $R^2$, $R^{2a}$, $R^3$, and $R^{3a}$ are independently selected from hydrogen and $C_1$–$C_{10}$ alkyl; with a hydroperoxide of the formula $R^1OOH$, wherein $R^1$ is $C_1$–$C_{10}$ allyl; in the presence of an effective amount of a substantially solid, insoluble, heterogenous acidic catalyst; followed by separation of the reaction mixture from said catalyst; wherein said catalyst has readily available acidity for organic reactions and exists in the solid phase in the processes of the invention, while the reactants in those processes, by contrast, exist in the liquid and/or gaseous phase, whence the catalyst is referred to as heterogeneous.

6 Claims, No Drawings

PREPARATION OF DIALKYL PEROXIDES

FIELD OF THE INVENTION

The present invention is in the field of organic synthesis relating to the production of dialkyl peroxides such as di-tert-butyl peroxide, and is particularly concerned with such methods involving the reaction of an alcohol such as tert-butyl alcohol and/or an olefin such as isobutylene with a hydroperoxide such as tert-butyl hydroperoxide in the presence of an acid catalyst. The present invention is more especially concerned with such a method of preparation wherein said acid catalyst is a heterogenous, essentially insoluble acidic catalyst with readily available acidity for organic reactions.

BACKGROUND OF THE INVENTION

The preparation of dialkyl peroxides by the reaction of an alcohol such as tert-butyl alcohol (t-BA) with an organic hydroperoxide such as tertiary hydroperoxide (t-BHP) is known. See, for example, U.S. Pat. Nos. 2,403,771; 2,862,973; and 3,6626,014. The preparation of dialkyl peroxides by the reaction of an olefin such as isobutylene with an organic hydroperoxide such as tBHP is also known. See Davies, et al., *J. Chem. Soc.,* 2200–2204, 1954. Also, French Pat. No. 1,555,308 shows the reaction of isobutylene with hydrogen peroxide to produce tBHP and di-tert-butyl peroxide. In such prior art processes, there have been employed soluble acid catalysts such as hydrogen bromide, sulfuric acid, soluble heteropoly acids, soluble isopoly acids and sulfonic acid resins having a high gel phase porosity, which also have a low degree of cross-linking and swell upon hydration, thereby reducing the amount of available acidity within such catalysts.

However, the use of such catalysts brings with it a number of serious disadvantages, including the high cost of the complex processing needed to recover the diallyl peroxide; the high cost of recovering the soluble catalyst; the pervasive cost, extensive corrosion, and significant safety hazards associated with the use of sulfuric acid; the use of boron-containing esters; the use of extraneous and environmentally undesirable solvents; and catalyst deactivation and deterioration, which is characteristic of catalyst resins. Canadian Pat. No. 839,312, for example, shows the production of di-tert-butyl peroxide by the reaction of t-BA and t-BHP using a gel-type 4% cross-linked resin, with the requirement that water be azeotropically removed, e.g., with chloroform, in order for the reaction to proceed. The use of heterogeneous acid catalysts with readily available acidity for organic reactions avoids all of the above-mentioned disadvantages.

Di-tert-butyl peroxide is a chemical agent and additive which has experienced a low volume of sales due to its high market price. This has resulted in a limitation on its current use for potentially a significant number of diverse specialty purposes. One of these purposes is in the manufacture of ethylene glycol (EG), a staple of commerce and a raw material for other end products, which has many end uses and is produced in immense quantities annually. Di-tert-butyl peroxide has been shown by the applicant herein to be highly effective and efficient in the production of ethylene glycol and propylene glycol (PG). See, e.g., U.S. Pats. Nos. 4,337,371; 4,393,252; 4,412,084; and 4,412,085. Ethylene glycol is a highly important article of worldwide commerce not only for its own properties, but for its role as well, when condensed with terephthalic acid on an equimolar amount, to produce polyethylene terephthalate (PET), from methanol alone and/or from methanol and formaldehyde.

In order for di-tert-butyl peroxide to find application and utility in the large scale manufacturing of ethylene glycol, or to become a successful candidate for other low cost uses such as in clean-burning diesel fuel as an very high cetane diesel fuel blending component, costly processing and purification reforms will have to be effected in the above-described production techniques for di-tert-butyl peroxide. Although methods have been suggested for the production and recovery of di-tert-butyl peroxide, as indicated, there remains considerable room for improvement in the efficiency and economics of the technology for producing di-tert-butyl peroxide. Unfortunately, the complex and costly processing methods which have been suggested in the prior art to date, cannot produce di-tert-butyl peroxide at a sufficiently low cost to permit its applicability to use in large volume, low cost methanol-based ethylene glycol and propylene glycol production, or to use as an very high cetane diesel fuel blending component.

SUMMARY OF THE INVENTION

In accordance with the present invention, there is provided a process for the preparation of a dialkyl peroxide comprising reacting one or more members selected from the group consisting of an alkylating alcohol of the formula ROH, and an olefin of the formula $(R^2)(R^{2a})C=C(R^3)(R^{3a})$, wherein R is $C_1$–$C_{10}$ alkyl, and $R^2$, $R^{2a}$, $R^3$, and $R^{3a}$ are independently selected from hydrogen and $C_1$–$C_{10}$ allyl; with a hydroperoxide of the formula $R^1OOH$, wherein $R^1$ is $C_1$–$C_{10}$ allyl; in the presence of an effective amount of a substantially solid, insoluble, heterogenous acidic catalyst; after which the reaction mixture is directly separated from the catalyst for use directly, or with a minimum of processing. The catalyst is reused, and once wholly or partially exhausted, can be regenerated in accordance with known procedures. In accordance with the present invention, when the catalyst is an acidic resin which has only a low degree of cross-linking, the hydroperoxide is reacted primarily with olefin reactant in order to maintain the available acidity, which is deactivated by the deleterious effect of water on it, and thus on the process and end product.

Particularly, in accordance with the present invention there is provided a process for the preparation of di-tert-butyl peroxide comprising reacting one or more members selected from the group consisting of tert-butyl alcohol and iso-butylene; with tert-butyl hydroperoxide; in the presence of an effective amount of a substantially solid, insoluble, heterogenous acid catalyst. Similarly, there is also provided a process for the preparation of di-tert-amyl peroxide comprising reacting one or more members selected from the group consisting of tert-amyl alcohol and tert-amylene; with tert-amyl hydroperoxide; in the presence of an effective amount of a substantially solid, insoluble, heterogenous acid catalyst.

The processes of the present invention described above, are also those wherein the substantially solid, insoluble, heterogenous acid catalyst comprises an at least 10% cross-linked ion exchange resin catalyst. The processes of the present invention further include those wherein the substantially solid, insoluble, heterogenous acid catalyst is an at least 20% cross-linked polystyrene-divinyl benzene acidic resin catalyst.

In accordance with the present invention there is further provided a process for the preparation of a diallyl peroxide comprising reacting one or more members selected from the group consisting of olefins of the formula $(R^2)(R^{2a})C=C(R^3)(R^{3a})$, wherein $R^2$, $R^{2a}$, $R^3$, and $R^{3a}$ are independently selected from hydrogen and $C_1$–$C_{10}$ alkyl; with a hydroperoxide of the formula $R^1OOH$, wherein $R^1$ is $C_1$–$C_{10}$ alkyl; in the presence of an effective amount of a substantially solid, insoluble, heterogenous acidic catalyst; followed by separation of the reaction mixture from said catalyst.

The process recited immediately above includes particularly a process for the preparation of di-tert-butyl peroxide comprising reacting iso-butylene with tert-butyl hydroperoxide in the presence of an effective amount of an at least 10% cross-linked acidic ion exchange resin catalyst. Similarly, there is further included particularly the process for the preparation of di-tert-amyl peroxide comprising reacting tert-amylene with tert-amyl hydroperoxide in the presence of an effective amount of an at least 10% cross-linked acidic ion exchange resin catalyst.

DETAILED DESCRIPTION OF THE INVENTION

The process of the present invention can be represented by the following equations:

$$ROH + R^1OOH \rightarrow ROOR^1 + H_2O \quad (1)$$

where the alkylating alcohol is the reactant; and

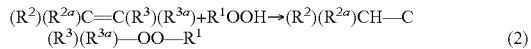

$$(R^2)(R^{2a})C=C(R^3)(R^{3a}) + R^1OOH \rightarrow (R^2)(R^{2a})CH-C(R^3)(R^{3a})-OO-R^1 \quad (2)$$

where an olefin is the reactant, and it can be seen that water is not a byproduct of the reaction.

In the above reactions, R is $C_1$–$C_{10}$ alkyl; $R^2$, $R^{2a}$, $R^3$, and $R^{3a}$ are independently selected from hydrogen and $C_1$–$C_{10}$ alky; and $R^1$ is $C_1$–$C_{10}$ alkyl. Preferably, R and $R^1$ are the same and are tertiary allyl group having 4 or 5 carbon atoms, i.e., tert-butyl or tert-amyl groups. There results from this choice of substituents a symmetrical dialkyl peroxide. It is also preferred that $R^3$ and $R^{3a}$ are independently hydrogen or allyl having 1 or 2 carbon atoms, and that $R^2$ and $R^{2a}$ are both hydrogen.

In a preferred embodiment of the present invention, di-tert-butyl peroxide is prepared by the reaction of tert-butyl hydroperoxide with tert-butyl alcohol or iso-butylene, or a mixture of both. In an analogous manner, di-tert-amyl hydroperoxide is preferably prepared by the reaction of tert-amyl hydroperoxide with tert-amyl alcohol or tert-amylene, or a mixture of both. Asymmetrical alkyl peroxides, i.e., where the allyl groups are different, such as tert-butyl tert-amyl peroxide, can be prepared by reacting, e.g., tert-amyl alcohol and/or tert-amylene with tert-butyl hydroperoxide. Ethyl tert-butyl peroxide can be prepared by reacting ethanol with tert-butyl hydroperoxide, and a mixture of different alkyl peroxides can be prepared by reacting a mixture of alkylating alcohols with tert-butyl hydroperoxide.

In carrying out the process of the present invention, it is generally desirable to provide at least 0.5 mol of alcohol(s) and/or olefin(s) per mol of hydroperoxide in the reaction. Preferably, at least 1 mol of alcohol(s) and/or olefin(s) per mol of hydroperoxide is employed; and potentially it is possible to employ up to about 10 mols of alcohol(s) and/or olefin(s) per mol of hydroperoxide. The use of alcohol(s) and/or olefin(s) in at least equimolar amounts relative to the hydroperoxide provides good reaction rates and high conversions of the reactants to final product.

Where an inorganic heterogenous solid acidic catalyst is employed, the reaction comprising the process of the present invention can be carried out using either alcohol(s) or olefin(s) to react with the hydroperoxide. Preferably, however, mixtures of 0.1 to 10 mols of alcohol(s) per mol of olefin(s) are employed. Where a highly cross-linked acidic resin catalyst is employed, the reaction can be carried out using either alcohol(s) or olefin(s) to react with the hydroperoxide. Preferably, however, mixtures of 0.1 to 10 mols of alcohol(s) per mol of olefin(s) are employed. Where the catalyst does not have a high degree of cross-linking, the reaction is carried out using olefin(s) as a primary reactant with the hydroperoxide. However, mixtures containing up to about 1.0 mol of alcohol(s) per mol of olefin(s) may be employed.

Olefin mixtures such as are used in the alkylation of methanol are particularly useful as alkylating agents for tBHP, which is kinetically from 10 to 20 times more reactive than methanol. The use of such olefin mixtures and the economic advantages flowing from such use are well known in the art, and include the coproduction of 1-butene. Such useful mixtures are readily obtainable from refinery streams, as well as from normal butane through a series of isomerization and dehydrogenation reactions.

The process of the present invention is carried out at temperatures sufficiently high to ensure a satisfactory reaction rate but not so high as to cause substantial decomposition of the hydroperoxide. Generally, the temperatures which are employed will range from about 20° C. to about 150° C., and preferably from about 40° C. to about 110° C. Because of the greater stability under thermal and catalytic conditions of di-tert-butyl peroxide compared to tert-butyl hydroperoxide, one of the preferred embodiments of the present invention is to carry out a continuous process in which the reaction is started at a lower temperature and finished at a higher temperature, such as occurs in an adiabatic process. The reaction takes place in the liquid phase, and the system pressure is maintained at a level sufficient to ensure such a liquid phase reaction. Pressures in the range 0.2 to 100 atmospheres gauge are characteristic.

An essential part of the process of the present invention is the use of an active heterogenous acid catalyst such as an acidic ion exchange resin which is highly cross-linked, by which is meant that it is at least 10% cross linked, whereby it is rendered oxidation resistant and hydrophobic as a catalyst. Surprisingly, it has been found possible, by using such catalysts, to eliminate the need for water removal, which has heretofore always been required. It has also been found that alkylating alcohols can be used to react with the hydroperoxide, as well as olefins.

The acid resins which may be employed in carrying out the process of the present invention are, e.g., polystyrene-divinyl benzene resins which are at least 10% cross-linked. As used herein, the degree of cross-linking refers to the use of sufficient cross-linking agent, e.g. divinyl benzene, to react with the designated percentage of the benzylic hydrogens of the polystyrene. For example, a 50% cross-linked polystyrene-divinyl benzene resin contains divinyl benzene in an amount sufficient to react with 50% of the polystyrene benzylic hydrogens. In large-scale structure these resins are macroreticular and possess physical porosity. The active sites, e.g., $SO_3H$, are accessible to the components of the reaction mixture without the necessity of substantial swelling. This is in complete contrast to the gel-type resins such as the Dowex 50WX4 used in the above-cited Canadian Pat. No. 839,312. These latter resins have high gel phase porosity and undergo substantial swelling upon hydration, whereupon they become deactivated with respect to acidity.

In practice of the invention sufficient of the heterogenous solid acid catalyst is employed to ensure a satisfactory conversion and selectivity. It is generally advantageous to contact the reactants with a bed of the solid catalyst, although other techniques such as slurry contact can be used. The solid catalyst may be contained to avoid contact with reactor surfaces, in order to avoid corrosion and contamination. Continuous procedures are preferred for carrying out the process of the present invention, although batch techniques can be used as well. A highly acidic macroreticular resin is a preferred heterogenous catalyst for the present invention and may be used advantageously in any of the embodiments taught or used for alkylation of methanol to methyl tert-butyl ether (Mt-BE).

In a preferred embodiment of the invention, iso-butane oxidate, which is produced in accordance with known oxidation procedures and which is comprised mainly to t-BA and t-BHP, after removal of unreacted iso-butane, is directly reacted to form di-tert-butyl peroxide in accordance with the present invention. Typical methods and conditions for the iso-butane oxidation are described in U.S. Pats. Nos. 2,845,461; 3,478,108; and 4,408,081.

As described, one of the critical features of the methods of preparation of the present invention resides in the acid catalyst, which is a heterogenous, essentially insoluble acidic catalyst with readily available acidity for organic reactions. The term "heterogeneous" as used herein, refers to the fact that the catalyst exists in the solid phase in the processes of the present invention, while the reactants in those processes, by contrast, exist in the liquid and/or gaseous phase. The catalysts thus carry out their function in this "heterogeneous" manner, involving different phases. The acidic catalyst is, e.g., an acid resin, zeolite, silica-alumina, insoluble inorganic acid or synthetic heterogenous acid catalyst. The preparation of synthetic heterogenous acid catalysts of variable chemical composition is described in U.S. Pat. Nos. 3,220,959 and 3,274,120. Other types of heterogenous acid catalysts may also be made by coprecipitation of different metal compounds to yield mixed metal oxide heterogenous catalysts with a large number of active acid sites. The coprecipitation technique when applied to metals with different diameters and different valence states prevents the formation of well-ordered metal oxides. With such metal oxides, a large number of surface acid sites are in such a position that they cannot be dehydrated even at high temperatures.

As a result of the symmetry of di-tert-butyl peroxide, it is a particularly efficient free radical generating peroxide. Di-tert-butyl peroxide of high purity can be employed for its currently limited applications and can be produced for those purposes in accordance with the processes of the present invention, when purified by known techniques. For large volume uses which will require a low production costs, such as for use as a free radical generator in the production of ethylene glycol from methanol, or ethylene glycol from methanol and formaldehyde, or as an very high cetane (Cetane No. $\geq 1500$) improver for diesel fuel, certain constraints imposed by commercial reality must be recognized. For these uses overall processing must be simple and low in capital cost. Accordingly, the reacting hydroperoxide need not be totally converted, because the hydroperoxide itself is a free radical generator, albeit a much less efficient one than peroxide. Thus, the reaction effluent should be usable directly or with minimal after processing and should not contain potentially deleterious materials such as corrosive acid catalyst and the like. depending upon expected use.

DESCRIPTION OF PREFERRED EMBODIMENTS

The following examples are presented by way of illustration of the present invention, and are not, nor intended to be in any way a limitation of the present invention.

EXAMPLE 1

A series of reaction runs was carried out in accordance with the present invention. In each case a dry Amberlyst A-15 resin was employed. The Amberylst A-15 is a strong acid ion exchange resin of the sulfonic acid type with the type macroreticular structure that is essential for carrying out the reactions which comprise the processes of the present invention. The dry resin was prepared by repeated washings with acetone, followed by draining of the acetone and vacuum drying of the resin at 60° to 80° C.

EXAMPLE 2

A reaction mixture with a minimal excess of alkylating component t-BA of 10 g of t-BA and t-BHP in a molar ratio of 1.5:1.0 was reacted in the presence of 5 g of dry acid resin for 1 h at 70° C. The conversion of t-BHP was 75 to 78% and at a very high selectivity for di-tert-butyl peroxide. The liquid effluent separated from the resin was usable for the free radical dehydrodimerization of methanol for production of ethylene glycol.

EXAMPLE 3

A reaction mixture with a minimal excess of alkylating component t-BA, of 10 g of t-BA and t-BHP in a molar ratio of 105:1.0 was reacted in the presence of 5 g of dry acid resin for 2 h at 70° C. The conversion of t-BHP was 88 to 90% at a very high selectivity to di-tert-butyl peroxide. The liquid effluent separated from the resin is usable for the free radical induced addition of methanol to formaldehyde for production of ethylene glycol. From an equimolar amount of t-BHP, the amount of ethylene glycol formed after alkylation, in accordance with the procedures described herein, is over 20 times the amount of ethylene glycol formed by using t-BHP directly without alkylation.

EXAMPLE 4

A reaction mixture with a minimal excess of alkylating component t-BA of 10 g of t-BA and t-BHP in a molar ratio of 1.05:1.0 was reacted in the presence of 5 g of dry acid resin for 2 h at 70° C. and 1 h at 80° C. The conversion of t-BHP was very high from at least 97 up to essentially 100% at a very high selectivity to di-tert-butyl peroxide. The liquid effluent separated from the resin is usable for a variety of free radical dehydrodimerizations.

EXAMPLE 5

A reaction mixture with a modest excess of alkylating component t-BA of 10 g of t-BA and t-BHP in a molar ratio of 1.25:1.0 was reacted in the presence of 5 g of dry acid resin for 1 h at 70° C. The conversion of t-BHP was 85 to 87% at a very high selectivity to di-tert-butyl peroxide. The liquid effluent separated from the resin is usable for the free radical dehydrodimerizations of methanol for production of ethylene glycol.

EXAMPLE 6

A reaction mixture with a modest excess of alkylating component t-BA of 10 g of t-BA and t-BHP in a molar ratio of 1.25:1.0 was reacted in the presence of 5 g of dry acid resin for 2 h at 70° C. The conversion of t-BHP was 97 to up to 100% at a very high selectivity to di-tert-butyl peroxide. The liquid effluent separated from the resin is usable for the free radical induced addition of methanol to formaldehyde for production of ethylene glycol.

EXAMPLE 7

A reaction mixture with a modest excess of alkylating component t-BA containing ethanol, methanol and water, such as a representative stream available from the di-tert-butyl peroxide free radical induced addition of methanol to formaldehyde for production of ethylene glycol, of 10 g of t-BA:t-BHP:EtOH:MeOH:$H_2O$ in a molar ratio of 1.25:1.00:0.19:0.28:0.50 was reacted in the presence of 5 g of dry acid resin for 1 h at 70° C. The conversion of t-BHP was 82 to 85% at a very high selectivity to di-tert-butyl peroxide. The liquid effluent separated from the resin is usable as a feed for the free radical induced addition of methanol to formaldehyde for production of ethylene glycol.

EXAMPLE 8

A reaction mixture with a modest excess of alkylating component t-BA containing ethanol, methanol and water, such as a representative stream available from the di-tert-butyl peroxide free radical induced addition of methanol to formaldehyde for the production of ethylene glycol, of 10 g of t-BA:t-BHP:EtOH:MeOH:$H_2O$ in a molar ratio of 1.25:1.00:0.19:0.28:0.50 was reacted in the presence of 5 g of dry acid resin for 2 h at 70° C. The conversion of t-BHP was from 95% up to 100%, at a very high selectivity to di-tert-butyl peroxide. The liquid effluent separated from the resin is usable as a feed for the free radical induced addition of methanol to formaldehyde for production of ethylene glycol.

EXAMPLE 9

A reaction mixture containing t-BHP, iso-butylene and t-BA at molar ratios of 1.0:1.23:0.49 was continuously pumped into a pressurized 316 stainless steel reactor with a ½ in diameter by 4 in height bed of dry Amberylst A-15 as catalyst, at a space velocity of 2.0/h, and with an inlet temperature of 60° C. The effluent shows that the t-BHP is essentially 100% converted and that the iso-butylene is about 81% converted. The liquid effluent is stripped of the unreacted iso-butylene and the resultant di-tert-butyl peroxide rich composition is usable for the free radical induced addition of methanol to formaldehyde for the production of ethylene glycol.

EXAMPLE 10

An iso-butane oxidate, stripped of iso-butane and some unquantitized light components, was mixed with iso-butylene to give an alkylation reaction mixture containing t-BHP, iso-butylene and t-BA at molar ratios of 1.0:1.26:0.55. This mixture was continuously pumped into a pressurized 316 stainless steel reactor with a ½ in diameter by 4 in high bed of dry Amberylst A-15 as catalyst at space velocity of 2.0/h with an inlet temperature of 60° C. The effluent shows that the t-BHP is essentially 100% converted and that the iso-butylene is about 79% converted. The liquid effluent is stripped of the unreacted iso-butylene and the resultant di-tert-butyl peroxide rich composition is usable for the free radical induced addition of methanol to formaldehyde for the production of ethylene glycol.

EXAMPLE 11

An iso-butane oxidate, stripped of iso-butane and some unquantitized light components, was mixed with a crude t-BA rich stream containing ethanol, methanol and water, such as a representative stream available from the di-tert-butyl peroxide free radical induced addition of methanol to formaldehyde for the production of ethylene glycol, to give an alkylation reaction mixture containing t-BA:t-BHP:EtOH:MeOH:$H_2O$ in a molar ratio of 1.30:1.00:0.11:0.17:0.30. This mixture was continuously pumped into a pressurized 316 stainless steel reactor with a ½ in diameter by 4 in high bed of dry Amberylst A-15 as catalyst at a space velocity of 1.0/h, with an inlet temperature of 75° C. The effluent shows that the t-BHP is about 95–98% converted and the resultant di-tert-butyl peroxide rich composition is usable for the free radical induced addition of methanol to formaldehyde for the production of ethylene glycol.

What is claimed is:

1. A process for the direct, economic preparation of ditertiary butyl peroxide comprising,
   a. reacting tertiary butyl hydroperoxide with tertiary butyl alcohol,
   b. without substantial water removal,
   c. at temperatures of 50 to 120 C,
   d. optionally with isobutylene,
   e. in the presence of an effective amount of an acidic, at least 10% cross-linked ion exchange resin catalyst, and
   f. removing the product effluent from catalyst for use.

2. The process of claim 1 wherein the said resin is at least 20% cross-linked polystyrene-divinyl benzene acidic resin.

3. A process for the direct, economic preparation of ditertiary butyl peroxide comprising,
   a. reacting an isobutane oxidate containing tertiary butyl hydroperoxide and tertiary butyl alcohol,
   b. without substantial water removal,
   c. at temperatures of 50 to 120 C,
   d. optionally with added tertiary butanol and/or isobutylene,
   e. in the presence of an effective amount of an acidic, at least 10% cross-linked ion exchange resin catalyst, and
   f. removing the product effluent from catalyst for use.

4. The process of claim 3 wherein the said resin is at least 20% cross-linked polystyrene-divinyl benzene acidic resin.

5. A process for the direct, economic preparation of ditertiary butyl peroxide which comprises,
   a. reacting an isobutane stripped isobutane oxidate containing 30 to 75 weight % tertiary butyl hydroperoxide and tertiary butanol,
   b. without substantial water removal,
   c. at temperatures of 50 to 120 C,
   d. optionally with added tertiary butanol and/or isobutylene,
   e. in the presence of an effective amount of an acidic, at least 10% cross-linked ion exchange resin catalyst, and
   f. removing the product effluent from catalyst for use.

6. The process of claim 5 wherein the said resin is at least 20% cross-linked polystyrene-divinyl benzene acidic resin.

* * * * *